US008824638B2

(12) United States Patent
Nicholson et al.

(10) Patent No.: US 8,824,638 B2
(45) Date of Patent: Sep. 2, 2014

(54) SYSTEMS AND METHODS FOR MAKING AND USING MULTI-BLADE COLLIMATORS

(75) Inventors: Bret D. Nicholson, Salt Lake City, UT (US); David Barker, Salt Lake City, UT (US)

(73) Assignee: General Electric Company, Schenectady, NY (US)

(*) Notice: Subject to any disclaimer, the term of this patent is extended or adjusted under 35 U.S.C. 154(b) by 90 days.

(21) Appl. No.: 13/211,944

(22) Filed: Aug. 17, 2011

(65) Prior Publication Data

US 2013/0044860 A1 Feb. 21, 2013

(51) Int. Cl.
*G21K 1/04* (2006.01)
*A61B 6/06* (2006.01)
*A61B 6/00* (2006.01)

(52) U.S. Cl.
CPC . *A61B 6/06* (2013.01); *A61B 6/487* (2013.01); *G21K 1/04* (2013.01)
USPC .......................................................... 378/150

(58) Field of Classification Search
CPC ............. A61B 6/06; G21K 1/04; G21K 1/046
USPC .......................................... 378/147, 148, 150
See application file for complete search history.

(56) References Cited

U.S. PATENT DOCUMENTS 3,919,467 A * 11/1975 Peugeot ........................ 378/98.2
4,875,225 A * 10/1989 Hunold .......................... 378/147
5,680,434 A * 10/1997 Thelosen et al. ............... 378/150
5,689,544 A * 11/1997 Van Den Besselaar ....... 378/150
2008/0267356 A1* 10/2008 Johnsen ........................ 378/152
2009/0074148 A1* 3/2009 Echner ........................... 378/152
2010/0054408 A1* 3/2010 Echner ........................... 378/150

FOREIGN PATENT DOCUMENTS

WO 96/27196 A1 9/1996
WO 2004/008968 A1 1/2004

OTHER PUBLICATIONS

Search Report and Written Opinion from PCT Application No. PCT/US2012/050222 dated Sep. 28, 2012.

* cited by examiner

*Primary Examiner* — Glenn Kao
(74) *Attorney, Agent, or Firm* — Kenneth E. Horton; Kirton McConkie (57) ABSTRACT

Systems and methods for making and using a multi-blade collimator device are described herein. The collimator device can include a base member, a rotational member, and multiple X-ray-attenuating blades that fit together to define an aperture. The blades are typically disposed between the base member and rotational member. Additionally, the blades can be mechanically connected to or interfaced with the base member and the rotational member so that when the rotational member is rotated with respect to the base member, the blades move and cause the aperture to change in size. The aperture can be any shape, including polygonal, square, or rectangular. While the aperture's size can be increased and decreased, the shape and orientation of the aperture can remain substantially constant. The collimator can contain a single layer of blades or multiple layers of blades. Other embodiments are described.

23 Claims, 14 Drawing Sheets

SYSTEMS AND METHODS FOR MAKING AND USING MULTI-BLADE COLLIMATORS

FIELD

This application relates generally to X-ray collimating devices. In particular, this application relates to systems and methods for providing a multi-blade collimator device that defines an adjustable aperture.

BACKGROUND

A typical X-ray imaging system comprises an X-ray source and an X-ray detector. The X-rays that are emitted from the X-ray source can impinge on the X-ray detector and provide an X-ray image of the object (or objects) that are placed between the X-ray source and the X-ray detector. In one type of X-ray imaging system, a fluoroscopic imaging system, the X-ray detector is often an image intensifier or, more recently, a flat panel digital detector.

In many medical imaging applications, a collimator is placed between the X-ray source and the X-ray detector to limit the size and shape of the field of the X-ray beam. The collimator can shape or limit the X-ray beam to an area of a patient's body that requires imaging. Accordingly, the collimator can prevent unnecessary X-ray exposure to areas surrounding the body part that is being imaged. By reducing the amount of X-ray exposure around the body part being imaged, the collimator may protect the patient from needless X-ray exposure. And because the collimator can limit the X-rays that hit the X-ray detector around the body part that is being imaged, the collimator can also help to improve image contrast and quality. For instance, by preventing excess X-rays from impinging on a flat panel digital detector, the collimator can help reduce or prevent image blooming or bleeding, which tends to occur when the detector is overloaded with X-rays. Thus, the collimator can minimize X-ray exposure and maximize the efficiency of the X-ray dosage to obtain an optimum amount of data for diagnosis.

SUMMARY

This application relates to systems and methods for making and using a multi-blade collimator device. Generally, the collimator device can include a base member, a rotational member, and multiple X-ray-attenuating blades that fit together to define an aperture. The blades are typically disposed between the base member and rotational member. Additionally, the blades can be mechanically connected to or interfaced with the base member and the rotational member so that when the rotational member is rotated with respect to the base member, the blades move and cause the aperture to change in size. The aperture can be any shape, including polygonal, square, or rectangular. While the aperture's size can be increased and decreased, the shape and orientation of the aperture can remain substantially constant. The collimator can contain a single layer of blades or multiple layers of blades.

BRIEF DESCRIPTION OF THE DRAWINGS

The following description can be better understood in light of the Figures, in which.

The Figures illustrate specific aspects of the described multi-blade collimator devices and methods for making and using such devices. Together with the following description, the Figures demonstrate and explain the principles of the structures, methods, and principles described herein. In the drawings, the thickness and size of components may be exaggerated or otherwise modified for clarity. The same reference numerals in different drawings represent the same element, and thus their descriptions will not be repeated. Furthermore, well-known structures, materials, or operations are not shown or described in detail to avoid obscuring aspects of the described devices. Moreover, for clarity, the Figures may show simplified or partial views, and the dimensions of elements in the Figures may be exaggerated or otherwise not in proportion.

DETAILED DESCRIPTION

The following description supplies specific details in order to provide a thorough understanding. Nevertheless, the skilled artisan would understand that the described multi-blade collimator devices and associated methods of making and using the collimator devices can be implemented and used without employing these specific details. Indeed, the described collimator devices and associated methods can be placed into practice by modifying the illustrated devices and methods and can be used in conjunction with any other apparatus and techniques conventionally used in the industry. For example, while the description below focuses on methods for making and using the collimator devices for use with any suitable X-ray imaging devices (such as mobile and stationary X-ray devices, including, without limitation, mini C-arm, standard C-arms, O-arms, compact style C-arms, non-circular arms, etc.), the described collimator devices can be used for any other suitable purpose, including for x-ray treatment procedures used in radiation therapy and/or for collimating gamma radiation used in nuclear medicine and/or for indicating the exposure size with a visible light source or laser.

In addition, as the terms on, attached to, connected to, or coupled to are used herein, one object (e.g., a material, a layer, a substrate, a member, etc.) can be on, attached to, connected to, or coupled to another object, regardless of whether the one object is directly on, attached, connected, or coupled to the other object or whether there are one or more intervening objects between the one object and the other object. Also, directions (e.g., foremost, rearmost, base, above, below, top, bottom, side, up, down, under, over, upper, lower, horizontal, vertical, x, y, z, etc.), if provided, are relative and provided solely by way of example and for ease of illustration and discussion and not by way of limitation. In addition, where reference is made to a list of elements (e.g., elements a, b, c), such reference is intended to include any one of the listed elements by itself, any combination of less than all of the listed elements, and/or a combination of all of the listed elements. Furthermore, as used herein, the terms a, an, and one may each be interchangeable with the terms at least one and one or more.

Figure 27:
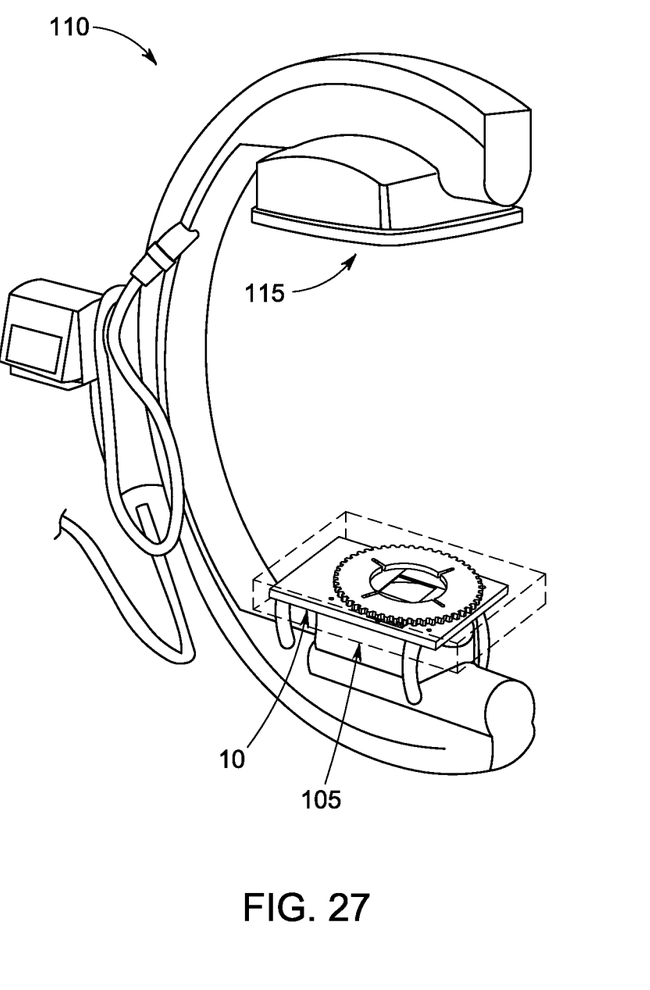
FIG. 27 shows a side schematic view of an X-ray machine comprising some embodiments of the multi-blade collimator.

As described above, this application discusses a collimator. While this collimator can perform any suitable function, FIG. 27 shows some embodiments in which the collimator 10 is used on a C-arm 110 to limit and define the shape and size of an x-ray beam (not shown) that is emitted from an x-ray source 105 (e.g., a standard X-ray source, a rotating anode X-ray source, a stationary or fixed anode X-ray source, a solid state X-ray emission source, a fluoroscopic X-ray source, etc.) towards an image detector (e.g., a flat panel detector 115, an image intensifier, etc.).

Figure 1:
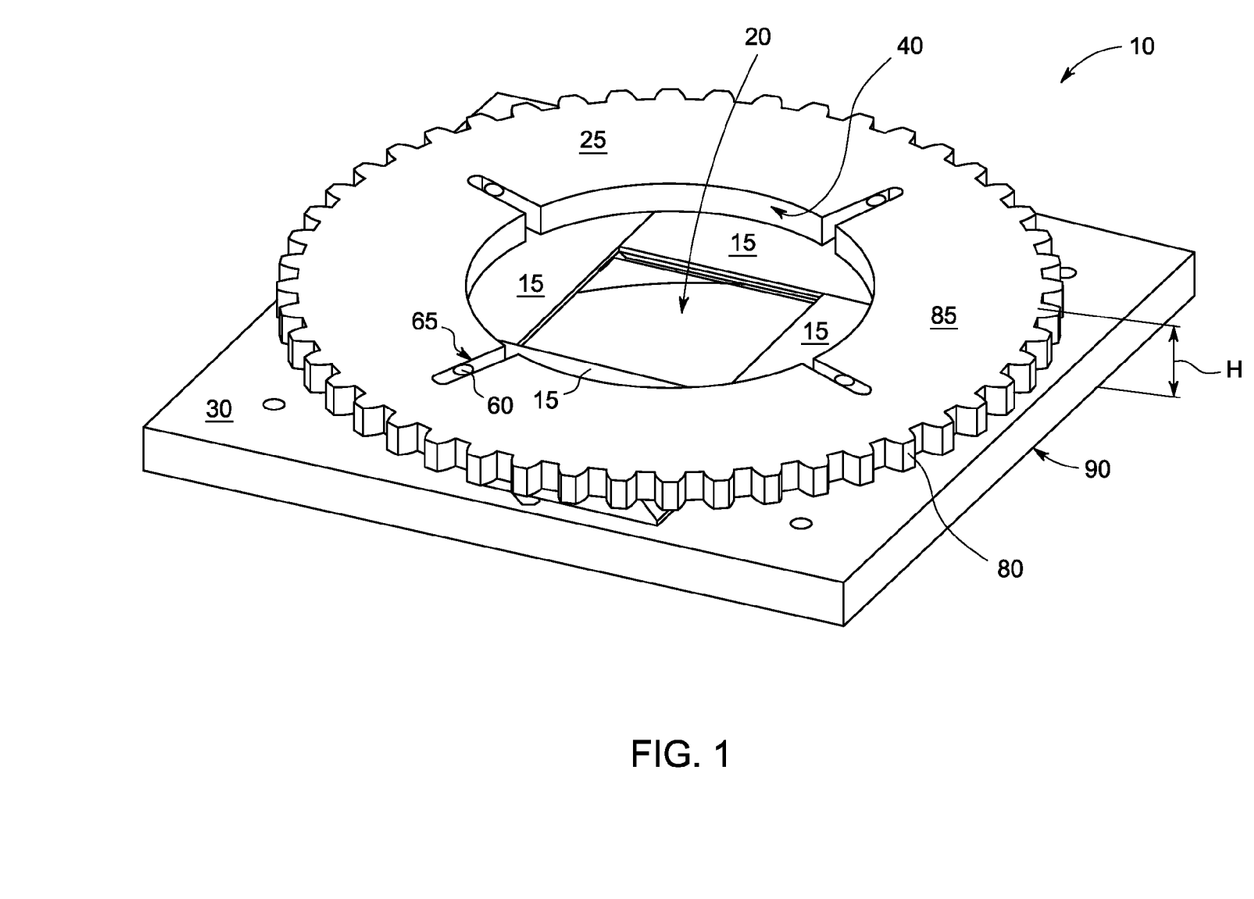
FIG. 1 shows a side perspective view of some embodiments of a multi-blade collimator device.
Figure 2:
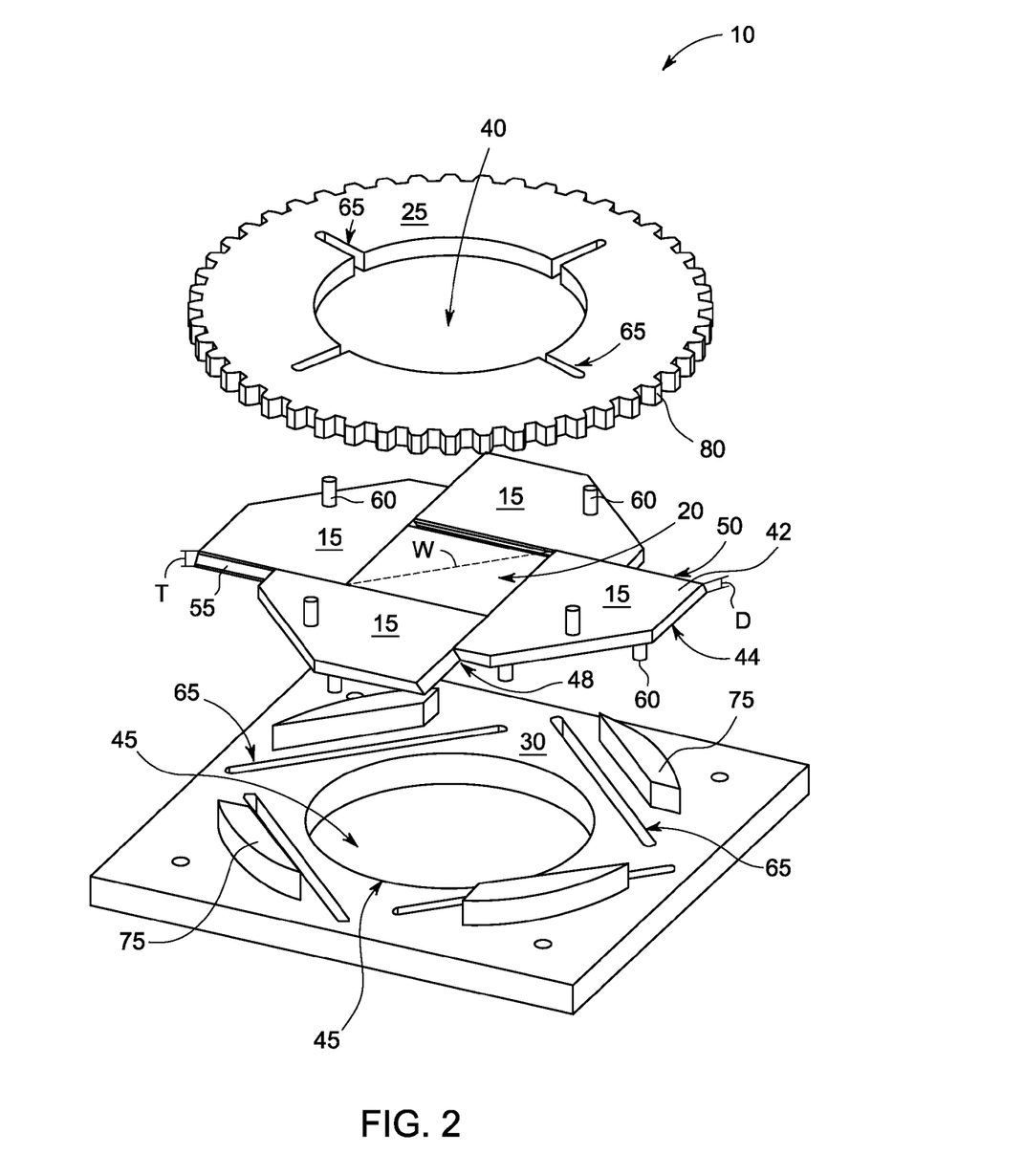
FIG. 2 shows an exploded view of some embodiments of the multi-blade collimator device.
Figure 3:
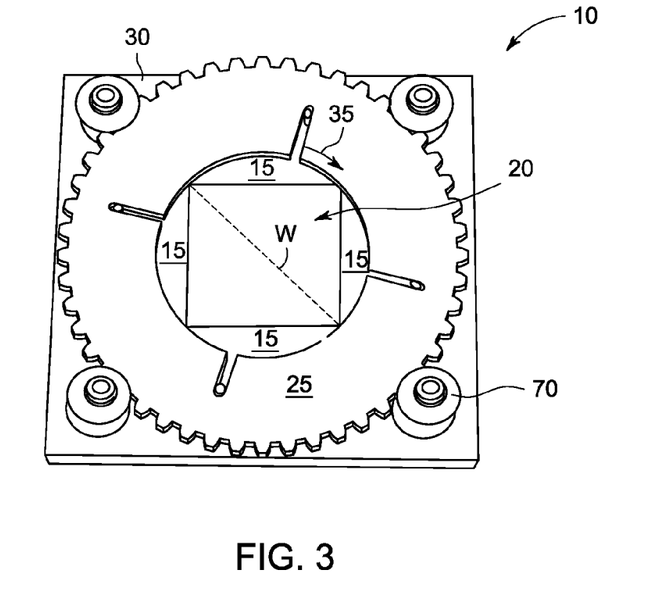
FIG. 3-5 show top schematic views of some embodiments of the multi-blade collimator device as an aperture in the device is re-sized.
Figure 4:
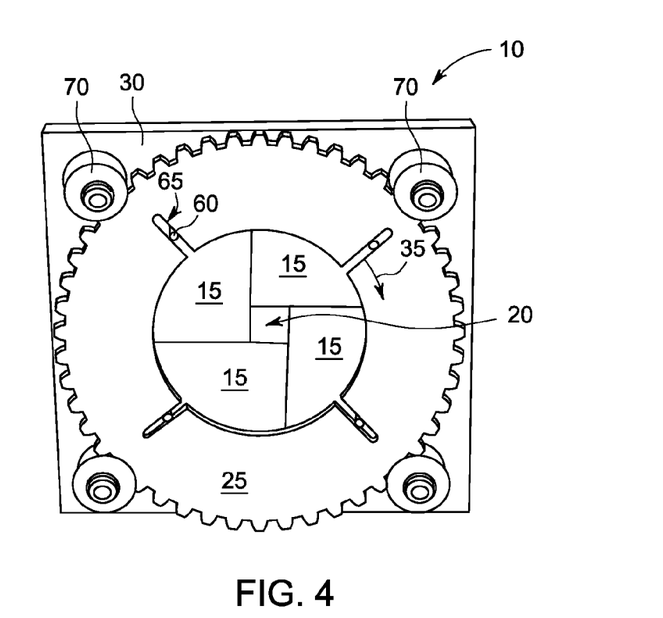
Figure 5:
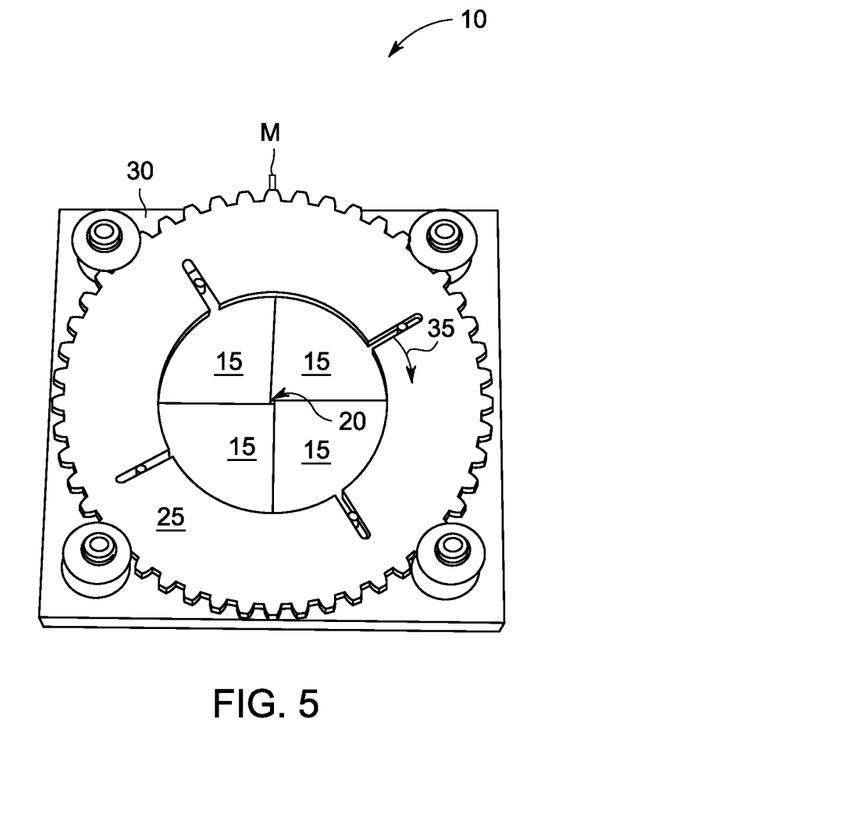
Figure 6:
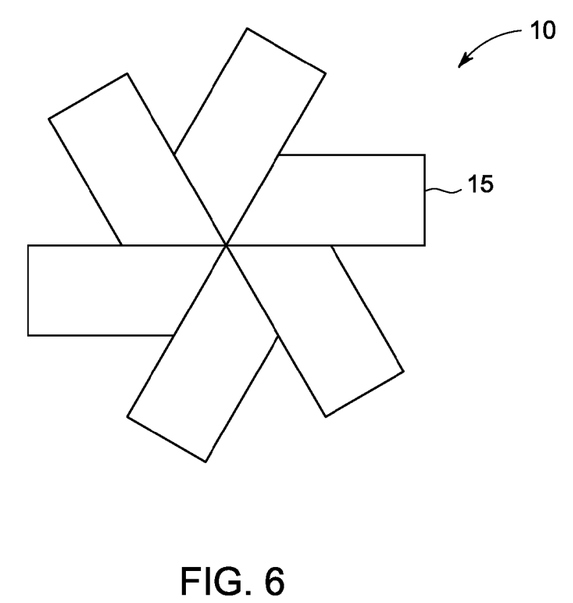
FIG. 6-10 each show a top schematic view of some embodiments of the multi-blade collimator device containing an aperture that is substantially hexagonal in shape.
Figure 7:
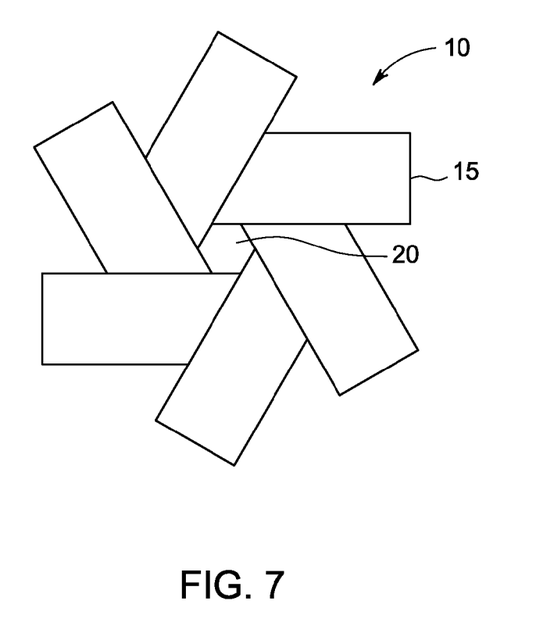
Figure 8:
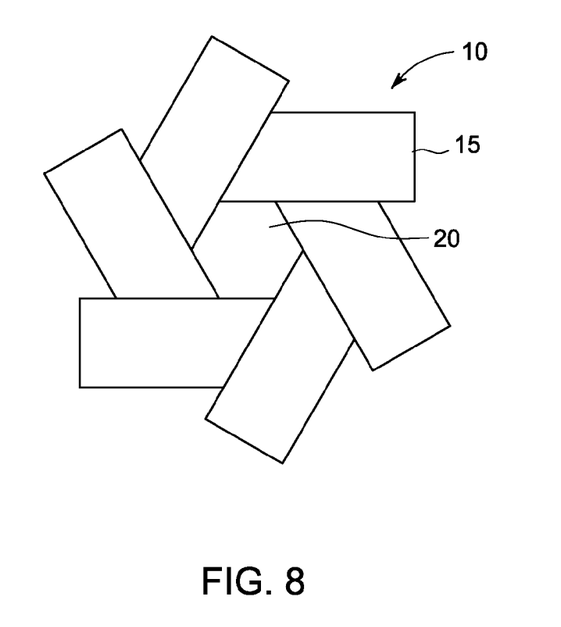
Figure 9:
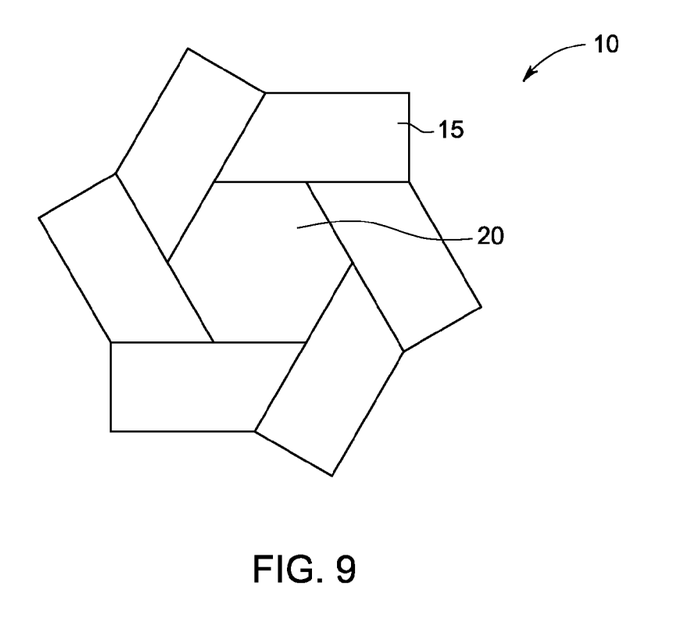
Figure 10:
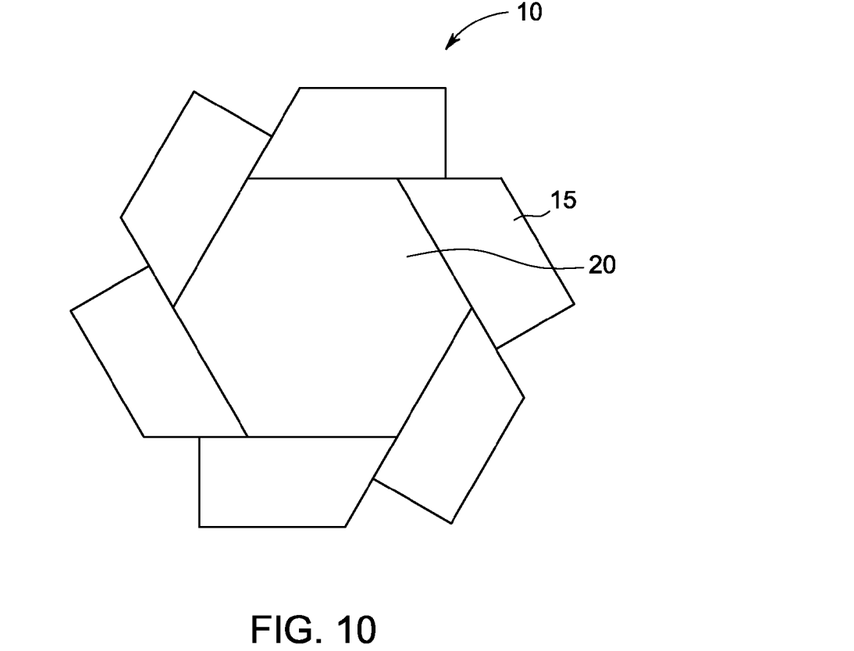
Figure 11:
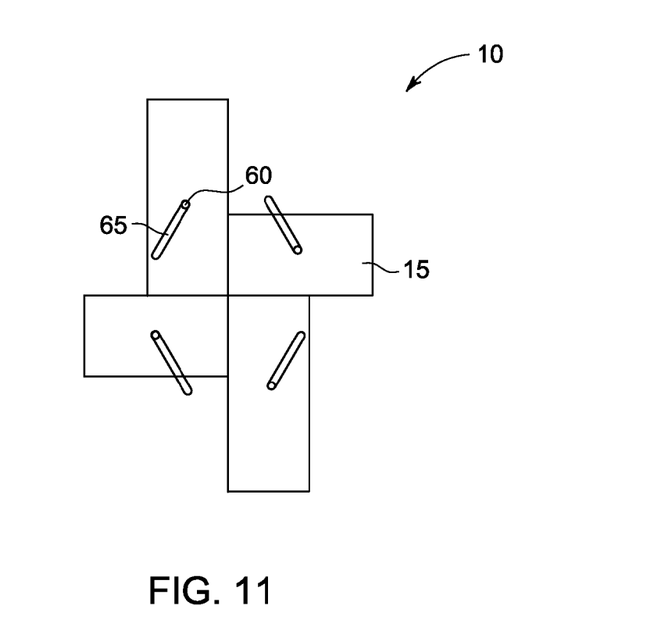
FIGS. 11-15 each show a top schematic view of some embodiments of the multi-blade collimator device containing an aperture that is substantially rectangular in shape.
Figure 12:
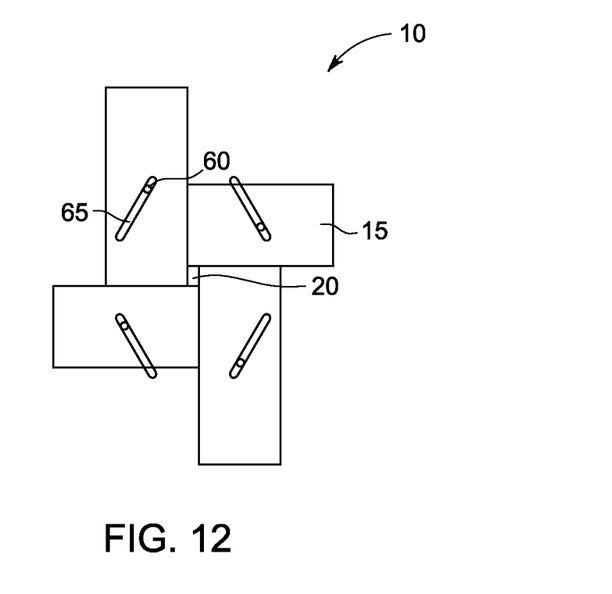
Figure 13:
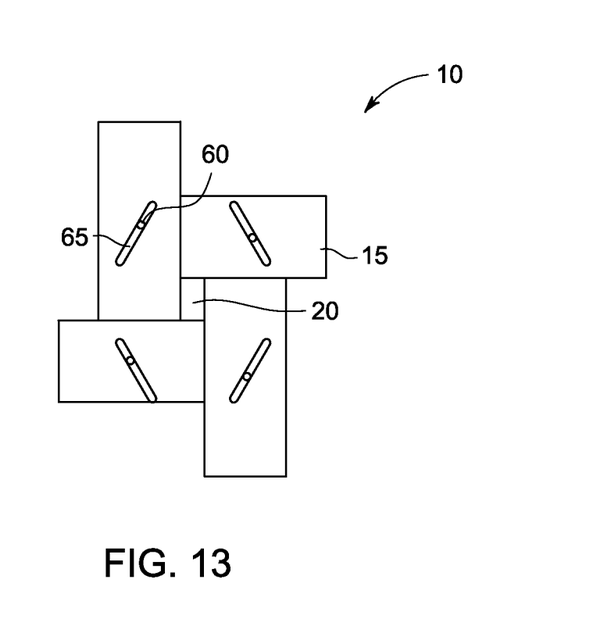
Figure 14:
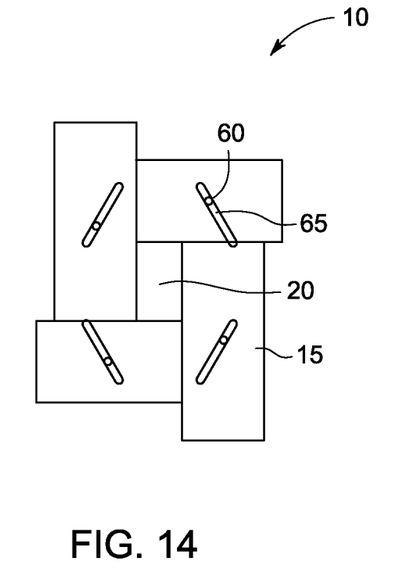
Figure 15:
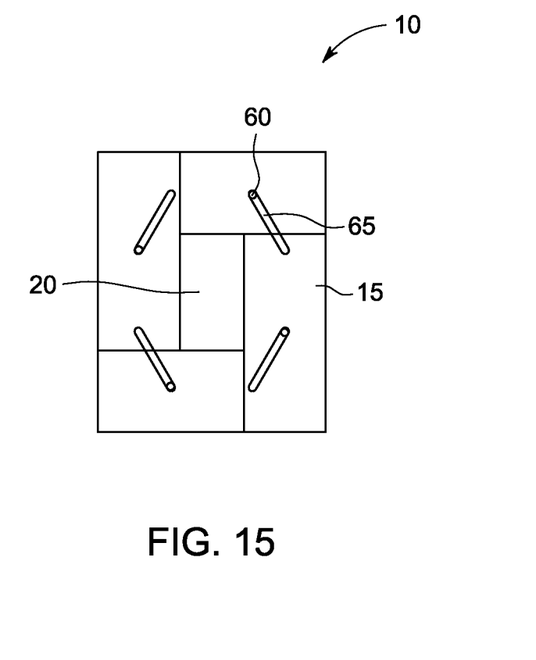

Some embodiments of the multi-blade collimator devices and associated methods of making and using these collimators are described herein and illustrated in the Figures. In particular, FIGS. 1 and 2 show some embodiments in which the multi-blade collimator device 10 comprises multiple X-ray-attenuating blades 15 that are situated to define an aperture 20. FIGS. 1 and 2 also show that the blades 15 can be at least partially disposed between a rotational member 25 and a base member 30. With such a configuration, FIGS. 3 through 5 illustrate that as the rotational member 25 rotates [e.g., in (or opposite to) the direction of arrow 35] with respect to the base member 30, the blades 15 can be forced to move with respect to each other and thereby change the size of the aperture 20.

The collimator 10 can comprise any number of X-ray-attenuating blades 15 that allows it to define the aperture 20 and to limit the size and/or shape of the field of an X-ray beam (not shown) that is emitted from an X-ray source. In some embodiments, the collimator comprises 2, 3, 4, 5, 6, 7, 8, 9, 10, . . . 20, or even more blades. By way of illustration, FIG. 2

The X-ray attenuating blades 15 can cause the aperture 20 to have any suitable shape. In one example, where the collimator comprises 2 blades, the aperture may have a substantially rectangular shape, with the length of the aperture being defined by the blades and the ends of the aperture being defined by the inner opening (e.g., 40 and/or 45) of the rotational 25 and/or base 30 members. In another example, where the collimator has 3 blades, the aperture can be substantially triangular in shape. In still another example, where the collimator comprises 4 blades, the aperture can comprise a parallelogram (e.g., substantially square as shown in FIG. 1 or substantially rectangular as shown in FIGS. 12 through 15). In yet other examples, where the collimator comprises 5, 6, 7, or 8 blades in a single layer (e.g., where no blade is stacked on another blade), the aperture can respectively be substantially polygonal in shape, including pentagonal, hexagonal (as shown in FIGS. 6 through 10), heptagonal, and octagonal in shape. Indeed, as the collimator can comprise any suitable number of blades, the aperture can have any polygonal shape with any number of sides—even to approach having a substantially circular appearance.

The blades 15 can cause the aperture 20 to be any suitable size or any suitable range of sizes. In some embodiments, the blades are adjustable so that the aperture has a maximum width W (e.g., a diagonal measurement from the aperture's furthest corners, as shown in FIG. 3) of about 0.5 millimeter ("mm"), about 1 centimeter ("cm"), about 5 cm, about 10 cm, about 20 cm, about 100 cm, or any desired width. In some embodiments, the aperture can have a maximum width between about 5 cm and about 46 cm (e.g., about 15 cm±2 cm). In other embodiments, the maximum width can be any suitable combination or sub-range of these amounts.

The collimator 10 can be configured so that the blades 15 can be adjusted so the aperture 20 has any suitable minimum width that allows the collimator to function as described. In some embodiments, the blades are adjustable so that the aperture has a minimum width M (e.g., a measurement between the two closest opposing edges of the aperture when the blades are moved as close together as the collimator will permit as shown in FIG. 5) of about 0.25 mm, about 1 cm, about 2 cm, about 3 cm, about 10 cm, about 20 cm, or any desired minimum amount. In some embodiments, the aperture can have a minimum width that is less than about 2 cm. In other embodiments, the aperture can be any suitable combination or sub-range of these minimum widths.

The X-ray attenuating blades 15 can comprise any suitable material that allows them to substantially prevent X-rays from passing through the blades. Some examples of suitable X-ray attenuating materials include tungsten, lead, gold, copper, tungsten-impregnated substrates (e.g., glass or a polymer impregnated with tungsten), coated substrates (e.g., glass or a polymer coated with tungsten, lead, gold, etc.), steel, aluminum, bronze, brass, rare earth metals, or combinations thereof. In some embodiments, however, the blades comprise tungsten.

The blades 15 can be any suitable thickness that allows them to substantially prevent X-rays from passing therethrough. In some embodiments, each blade has a thickness (illustrated as T in FIG. 2) of about 10 millimeters ("mm"), about 5 mm, about 3 mm, about 2 mm, about 1 mm, about 0.2 mm, or 0.1 mm. In some embodiments, each blade can be between about 1 and about 5 mm thick (e.g., about 3 mm thick±1 mm). In other embodiments, the thickness can be any suitable combination or sub-range of these amounts.

Figure 16:
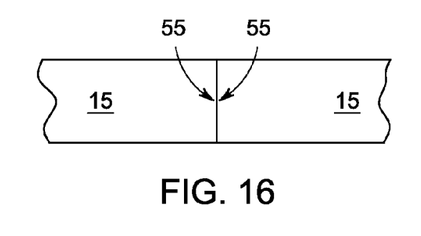
FIGS. 16-20 illustrate side views of some embodiments of connections between X-ray attenuating blades of the multi-blade collimator.
Figure 17:
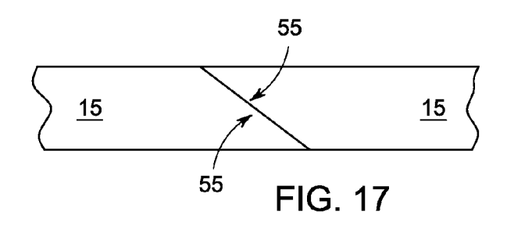
Figure 18:
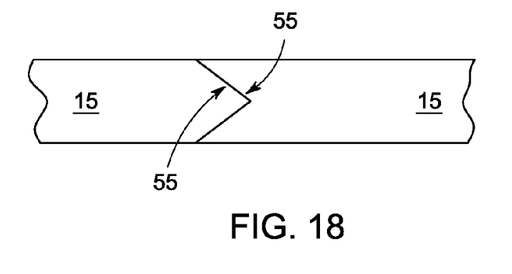
Figure 19:
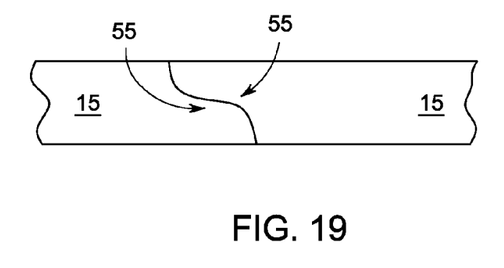
Figure 20:
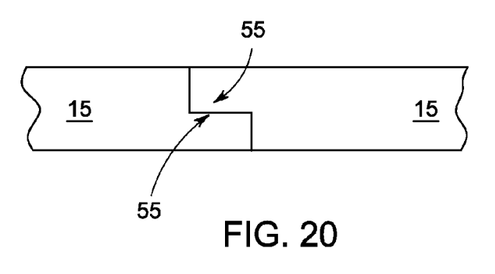
Figure 21:
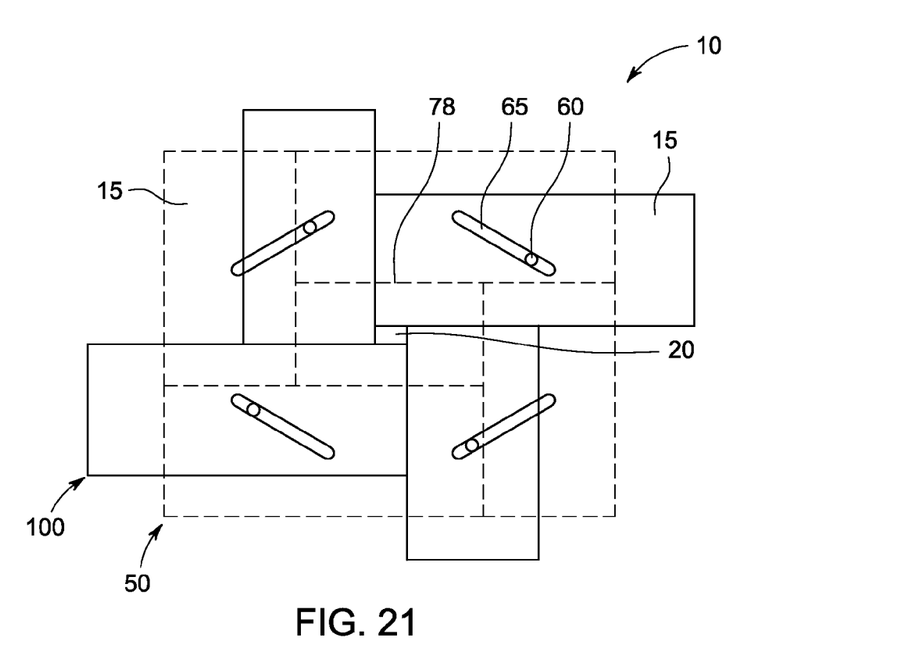
FIGS. 21-24 show top schematic views of some embodiments of the multi-blade collimator device that comprise multiple layers of blades with a four-sided aperture.

FIG. 2 shows that in some embodiments, the blades 15 form a single layer 50 in which the distance D between a foremost 42 and a rearmost 44 faces of the layer is substantially In some configurations, the edge of one blade 15 contacts an edge of one or more blades (e.g., 2 adjacent blades) to define the aperture 20. For example, the edges 55 may contact each other at a straight butt connection (as shown in FIG. 16) or through an interlocking connection in which a portion of one blade overlaps a corresponding portion on an adjacent blade. However, because some straight butt connections may allow X-rays to pass through a space between adjacent blades and/or may not help guide the blades in the proper manner, in some configurations the blades contact each other at overlapping connections to help ensure that X-rays do not pass between the contacting blades.

Where an edge 55 of one blade 15 overlaps an edge of one or more other blades, the blades can be configured so that the blades slide across each other and to define the aperture 20. FIGS. 17 through 20 show some examples of suitable overlapping connections in which the blade 15 edges 55 overlap each other at a mitered connection, a tongue-and-groove connection, an ogee connection, and a half-and-half connection. Similarly, FIG. 2 shows the blades 15 can contact each other with an ogee connection 48.

The rotational member 25 can be configured to that it drives the X-ray attenuating blades 15 closer together and further apart so as to adjust the size of the aperture 20. In some embodiments, the rotational member comprises an inner opening 40 that allows an X-ray beam to pass through the collimator 10 and to be resized and reshaped by the blades. Thus, this inner opening 40 can be any number of sizes or shapes. For example, the width (or diameter) of the rotational member's inner opening can be larger, smaller, or equal to the maximum width W of the aperture. In another example, the width of the rotational member's inner opening can be larger than or equal to the aperture's maximum width. And while the inner opening can be any suitable shape that allows the collimator to function as intended, FIG. 2 shows some embodiments in which the inner opening 40 is substantially circular in shape.

The rotational member 25 can be mechanically connected to the blades 15 in any manner that allows the rotation of the rotational member to force the blades to move and resize the aperture 20. In some embodiments, one or more guide members (e.g., pins, posts, rail guides, stand-offs, bearings, rails, etc.) can extend from the rotational member to one or more corresponding guide receptacles (e.g., grooves, slides, channels, rail guides, bearings, troughs, path, etc.) of each blade. In other embodiments, one or more guide members extend from each blade to one or more corresponding guide receptacles of the rotational member. By way of illustration, FIGS. 1 and 2 show some embodiments in which each blade 15 comprises a post 60 that is received by a corresponding channel 65 in the rotational member 25. FIGS. 3-5 illustrate that as the rotational member 25 rotates with respect to the base member 30, each post 60 is able to slide through its corresponding channel 65 so that the blades 15 are driven to change the size of the aperture 20.

The base member 30 can be configured to allow it to direct the movement of the blades 15 along a specified path as the rotational member 25 rotates. In some embodiments, the base member comprises an inner opening 45 (see FIG. 1) that allows an X-ray beam to pass through the collimator 10 and to be resized and reshaped by the blades 15. Thus, the base member's inner opening can be configured with any number of sizes or shapes. For example, the width (or diameter) of base member's inner opening can be larger, smaller, or equal to the maximum width W of the aperture 20. In another example, the width of the base member's inner opening can be larger than or equal to the aperture's maximum width. And while the base member's inner opening can be any suitable shape that allows the collimator 10 to function as intended, FIG. 2 shows some embodiments in which the base member's inner opening 45 is substantially circular in shape.

The base member 30 can be mechanically connected to the blades 15 so that it allows the base member to direct the movement of the blades as the rotational member 25 rotates. In some embodiments, one or more of the guide members can extend from the base member to one or more of the corresponding guide receptacles of each blade. In other embodiments, one or more guide members can extend from each blade to one or more corresponding guide receptacles of the base member. By way of illustration, FIG. 2 shows some embodiments in which each blade 15 comprises a plurality of posts 60 that can be received by a corresponding channel 65 in the base member 30. Thus, as the rotational member rotates, channels in the base member can dictate the angle and/or length of the path the blades will follow.

The base member 30 can be attached to the rotational member 25 so that it allows the rotational member to rotate with respect to the base member. For example, the collimator 10 can include one or more brackets, channels, internal spacers, washers, wheels, and/or other structures that are capable of coupling the rotational member to the base member. For example, FIG. 3 shows the base member 30 can comprise a plurality of washer brackets 70 that couple the rotational member 25 to the base member 30. In another example, FIG. 2 shows that the base member 30 can comprise one or more internal spacers 75 that can run in an internal groove (not shown) of the rotational member 25 to help direct the movement of, and center, the rotational member.

The collimator 10 can optionally comprise any other known component or feature that allows it to function as described herein. In some embodiments, instead of having a single layer 50 of blades 15 (as shown in FIG. 2), the collimator can comprise 2, 3, 4, 5, or more layers of blades. For example, FIGS. 21 through 26 show some embodiments in which the collimator 10 comprises a first 50 and second 100 layer of blades 15. The two layers 50 and 100 may be stacked on top of each other, as illustrated. In other embodiments, though, none of the blades in either layer is stacked on another blade of that same layer.

Where the collimator 10 comprises more than one layer of blades 15, in some embodiments the apertures (20 and 78) can defined by the blades in each layer can be the same or different shapes. For example, while the first layer 50 can define an aperture 20 having a square shape, the second layer 100 can define an aperture 78 having a substantially rectangular shape.

In some embodiments, the blades 15 in the first 50 and second 100 layers can be adjusted together. In other embodiments, the first and second layers of blades can be controlled and adjusted separately. For example, where the first layer defines a square aperture and the second layer defines a rectangular aperture, the aperture in the first layer could be opened to its maximum width in order to allow the aperture in the second layer to shape the field of the X-ray beam passing through the collimator 10.

In some embodiments, the apertures 20 and 78 defined by the first 50 and second 100 layers can have the same orientation. In other embodiments, the orientations of the apertures are offset by any desired amount. For example, where the aperture defined by the first layer is square and the aperture defined by the second aperture is also square and two apertures are offset by 45 degrees, the two apertures can be used to define an octagonal shape.

Figure 22:
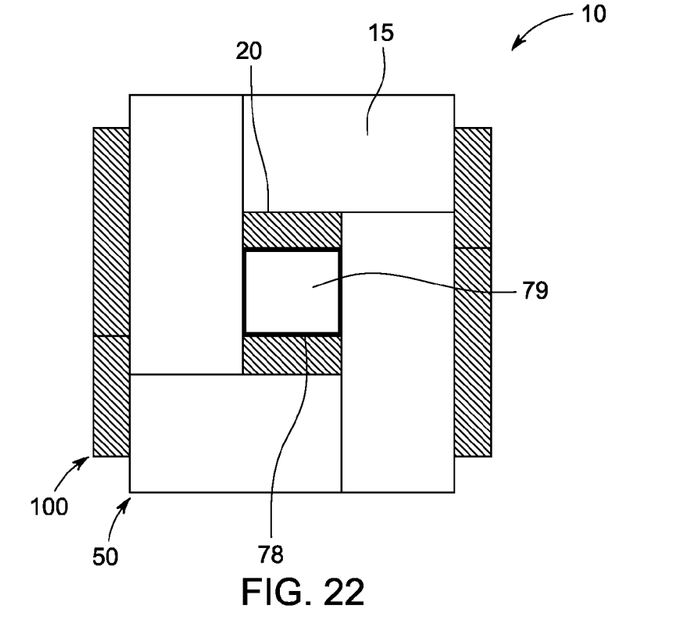
Figure 23:
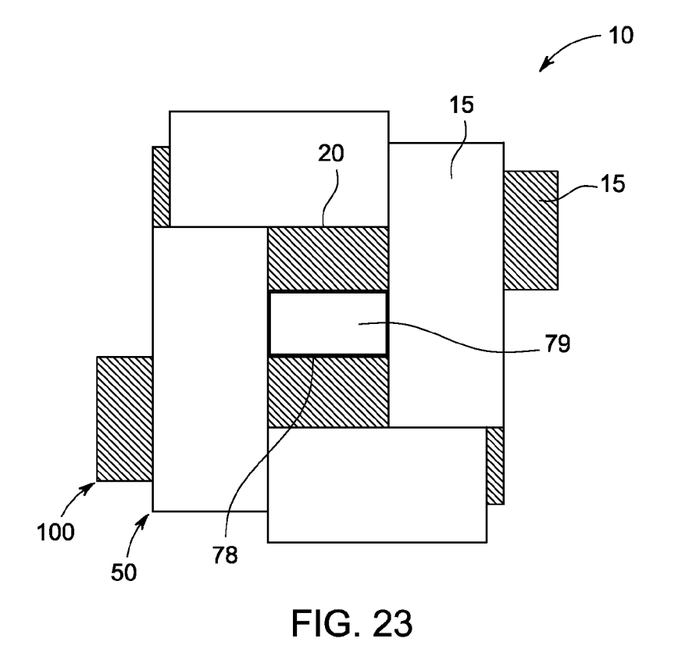
Figure 24:
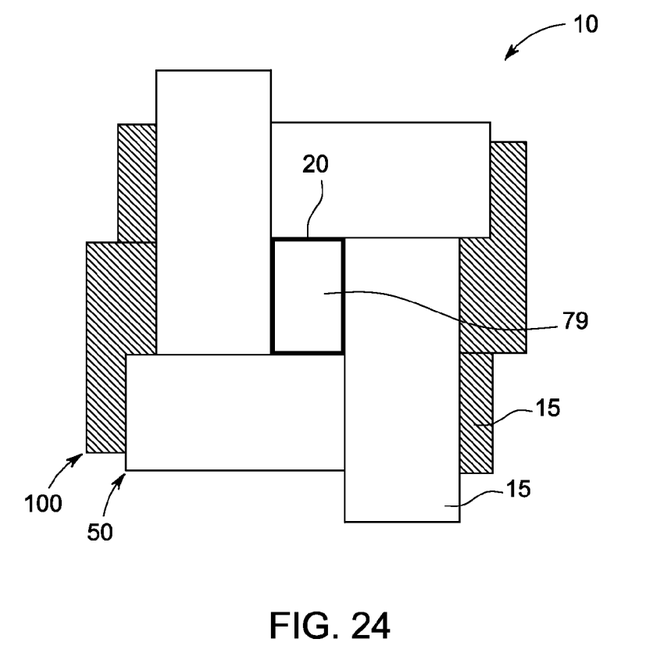

FIGS. 22 through 24 show some embodiments in which the first layer 50 defines a rectangular aperture 20 and the second layer 100 also defines a rectangular aperture 78, which is offset about 90 degrees from the orientation of the first aperture 20. Accordingly, the first 50 and second 100 layers can be used to define a third aperture 79 having a square shape. And FIGS. 23 and 24 show that the first 50 and second 100 layers aperture can also be used to define a third aperture having a substantially rectangular shape at different orientations.

Figure 25:
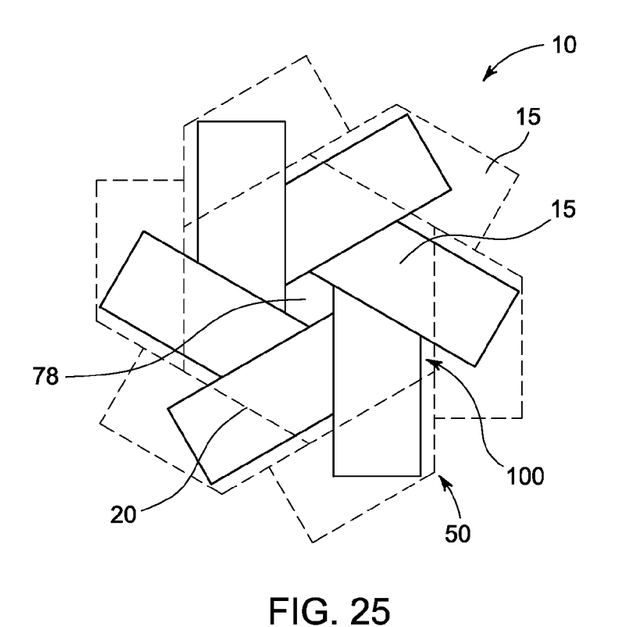
FIGS. 25-26 show top schematic views of some embodiments of the multi-blade collimator device that comprise multiple layers of blades with an aperture having six or twelve sides.
Figure 26:
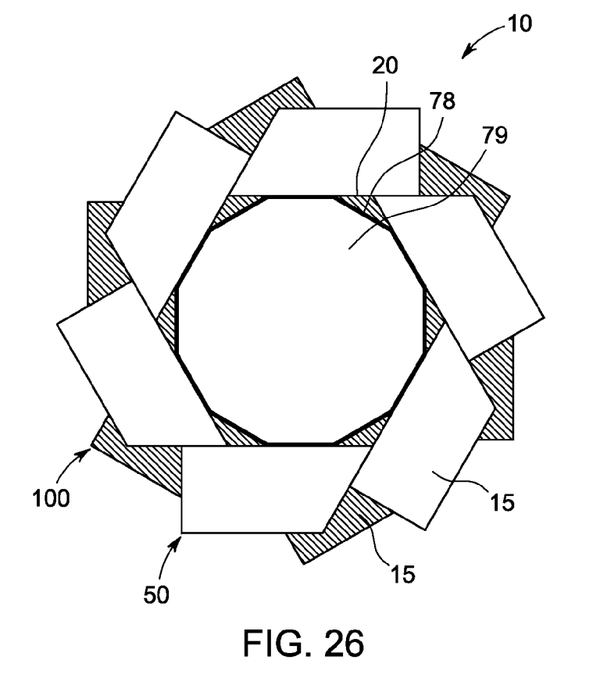

FIGS. 25 and 26 show some embodiments in which the first layer 50 and the second layer 100 each define a hexagonally-shaped aperture (20 and 78 respectively), which are offset from each other. Accordingly, as shown in FIG. 25, when the first layer 50 is opened wider than the second layer 100, the second layer's aperture can limit the X-ray beam (not shown) to a shape that is substantially hexagonal. By contrast, FIG. 26 shows that when the first 50 and second 100 layers are opened to substantially the same amount, the two layers can define the third aperture, which has a substantially dodecagonal shape.

The base member 30, rotational member 25, and other components of the described collimator 10 can be configured with any suitable material that allows the collimator to function as described. In some embodiments, the base member and/or rotational member include one or more metals (e.g., aluminum, iron, steel, copper, brass, bronze, etc.), ceramics, resins, polymers, graphite composite, glass composite, resinoids, or combinations thereof. Indeed, in some embodiments, the rotational member 25 and the base member 30 can comprise one or more plastic materials.

The multi-blade collimator 10 can be made in any manner that forms the structures described. By way of example, the collimator device can be formed through a process involving molding, injection molding, pressure forming, casting, cutting, etching, grinding, stamping, punching, extruding, drilling, welding, bonding, tapping, dying, screwing, and/or bending.

The multi-blade collimator 10 can have a wide variety of uses. In some embodiments, the rotational member 25 can be rotated to adjust the aperture 20 in any suitable manner, including manually and/or automatically. Where the rotational member 25 is rotated manually, it can be rotated as a user moves the rotational member with the user's hand, by sliding a slide that is coupled to a portion of the rotational member, through the use of a lever attached to the rotational member, an intermediate gear driving the rotational member, a magnetic field driving the rotational member, a timing belt driving the rotational member, or combinations thereof. Where the rotational member 25 is rotated automatically, it can be rotated through the use of or one or more motors (e.g., driving a gear that is meshed with teeth 80 from the rotational member, see FIG. 1), hydraulic actuators, pneumatic actuators, magnetic fields, linkages, and/or solenoids.

The multi-blade collimator 10 can be placed between the X-ray source and X-ray detector of any suitable X-ray device, including a mobile X-ray device (e.g., an X-ray device comprising a C-arm, a mini C-arm, O-arm, non-circular arms, etc.), and a fixed X-ray device. By way of illustration, FIG. 27 shows some embodiments in which the collimator 10 can be disposed near an enclosed X-ray source 105 on a C-arm 110 that also comprises a flat panel image detector 115.

The multi-blade collimator can have several useful features. First, unlike conventional collimators defining an aperture that is static in size, some embodiments of the aperture 20 are adjustable. Second, unlike some conventional collimators that stack collimating plates on top of each other (much like the shutter of a camera), some embodiments of the described collimator 10 comprise a single layer 50 of blades 15 in which no blade is stacked on another. Thus, the multi-blade collimator can be relatively thin. In some embodiments, the distance H (as shown in FIG. 1) between a front face 85 of the rotational member 25 and a rear face 90 of the base member 30 can be about 15 cm, about 10 cm, about 5 cm, about 2 cm, about 1 cm, about 0.5 cm, about 0.3 cm, about 1 mm, or 0.25 mm. In some embodiments, the overall thickness H of the collimator can be between about 0.5 cm and about 3 cm (e.g., less than about 2.5 cm; or about 1.3 cm±0.2 cm). In other embodiments, the overall thickness H can be any suitable combination or sub-range of these amounts.

A third feature is that some embodiments of the multi-blade collimator can be configured to limit the field of an X-ray beam to a shape that comprises 4 sides (e.g., a square or rectangle). Many conventional collimators are configured to limit the field of an X-ray beam to a shape that is circular, oval, or elliptical. Accordingly, such embodiments of the multi-blade collimator may be more appropriate for use with four-sided (e.g., square, rectangular, etc.), flat panel digital detectors.

A fourth feature is that while the orientation and/or shape of the aperture defined by some conventional collimators may change as the aperture is resized, some embodiments of the multi-blade collimator show that the aperture 20 can retain its orientation, shape, and proportions while being resized.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation, and use may be made without departing from the principles and concepts set forth herein. Also, as used herein, the examples and embodiments, in all respects, are meant to be illustrative only and should not be construed to be limiting in any manner.

The invention claimed is:

1. A multi-bladed collimator, comprising:
    a solid base member comprising an inner opening, the base member containing internal grooves adjacent internal spacers;
    a rotational member comprising an inner opening with channels extending radially from the inner opening; and
    multiple X-ray-attenuating blades that define an aperture, wherein the blades are mechanically connected to or interfaced with the base member and the rotational member using first guides on one side of the blades that are configured to fit in the grooves of the base member and second guides on an opposite side of the blades that are configured to fit in the channels of the rotational member so that when the rotational member rotates with respect to the base member, the aperture changes in size, wherein a single plane passes through all of the blades in the entire collimator and wherein an outer surface of the blades are configured to be contained by the internal spacers; and
    wherein the base member and the rotational member are located on opposite sides of the X-ray-attenuating blades.

2. The collimator of claim 1, wherein none of the blades are stacked on top of each other.

3. The collimator of claim 1, wherein the aperture comprises two or more edges.

4. The collimator of claim 3, wherein the aperture comprises four edges with a substantially square shape.

5. The collimator of claim 1, wherein a shape and orientation of the aperture remain substantially unchanged when the size of the aperture changes.

6. The collimator of claim 1, wherein a distance between a foremost face of the blades and a rearmost face of the blades is less than about 5 millimeters.

7. The collimator of claim 1, wherein the blades comprise a first layer of blades.

8. The collimator of claim 7, wherein the first layer of blades defines a first opening having a first shape in a first orientation.

9. A multi-bladed collimator, comprising:
    a rotational member comprising an inner opening with channels extending radially from the inner opening;
    a solid base member comprising an inner opening, the base member containing internal grooves adjacent internal spacers;
    multiple X-ray-attenuating blades that fit together to define an aperture, wherein the blades are at least partially disposed between the rotational member and the base member, wherein a single plane passes through all of the blades in the entire collimator and wherein an outer surface of the blades are configured to be contained by the internal spacers, and wherein the base member and the rotational member are located on opposite sides of the X-ray-attenuating blades;

a first set of guides extending between the base member and the blades, the first set of guides configured to fit in the grooves of the base member; and a second set of guides extending between the blades and the rotational member, the second set of guides configured to fit in the channels of the rotational member;

wherein the first and second set of guides direct the aperture to change in size when the rotational member rotates with respect to the base member.

10. The collimator of claim 9, wherein each of the blades abuts at its edges with at least two other blades.

11. The collimator of claim 9, wherein a distance between a foremost face of the blades and a rearmost face of the blades is less than about 5 millimeters.

12. The collimator of claim 9, wherein the collimator comprises four blades.

13. The collimator of claim 9, wherein a shape and orientation of the aperture remain substantially unchanged when the size of the aperture changes.

14. The collimator of claim 9, wherein the blades comprise a first layer of blades.

15. The collimator of claim 9, wherein the first layer of blades comprises a first shape.

16. The collimator of claim 9, wherein the aperture comprises a substantially square or rectangular shape.

17. An X-ray imaging device, comprising:
an X-ray source;
an X-ray detector; and
a multi-blade collimator containing:
  a rotational member comprising an inner opening with channels extending radially from the inner opening;
  a solid base member comprising an inner opening, the base member containing internal grooves adjacent internal spacers;
  multiple X-ray-attenuating blades that fit together to define an aperture, wherein the blades are at least partially disposed between the rotational member and the base member, wherein a single plane passes through all of the blades in the entire collimator and wherein an outer surface of the blades are configured to be contained by the internal spacers, and wherein the base member and the rotational member are located on opposite sides of the X-ray-attenuating blades;
  a first set of guides extending between the base member and the blades, the first set of guides configured to fit in the grooves of the base member; and
  a second set of guides extending between the blades and the rotational member, the second set of guides configured to fit in the channels of the rotational member;
wherein the first and second set of guides direct the aperture to change in size when the rotational member rotates with respect to the base member.

18. The device of claim 17, wherein each of the blades overlaps an edge of at least two other blades without increasing a thickness of a layer of the blades.

19. The device of claim 17, wherein a distance between a foremost face of the blades and a rearmost face of the blades is less than about 5 millimeters.

20. The device of claim 17, wherein the aperture comprises a substantially square or rectangular shape.

21. The device of claim 17, wherein a shape and orientation of the aperture remain substantially unchanged when the size of the aperture changes.

22. The device of claim 17, wherein the blades comprise a first layer of blades.

23. The device of claim 17, wherein the x-ray imaging device comprises a fluoroscopic imaging device.

* * * * *